(12) United States Patent
Raghuraman et al.

(10) Patent No.: US 7,339,160 B2
(45) Date of Patent: Mar. 4, 2008

(54) APPARATUS AND METHOD FOR ANALYSING DOWNHOLE WATER CHEMISTRY

(75) Inventors: Bhavani Raghuraman, Wilton, CT (US); Anthony Robert Holmes Goodwin, Sugar Land, TX (US); Oliver Clinton Mullins, Ridgefield, CT (US); Philip Andrew Rabbito, Milford, CT (US); Li Jiang, Ridgefield, CT (US); Timothy Gareth John Jones, Cottenham (GB); Andrew Loris Kurkjian, Sugar Land, TX (US); Gale Hyslip Gustavson, Brookfield, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 10/532,578

(22) PCT Filed: Nov. 19, 2003

(86) PCT No.: PCT/GB03/05016

§ 371 (c)(1),
(2), (4) Date: Nov. 4, 2005

(87) PCT Pub. No.: WO2004/048969

PCT Pub. Date: Jun. 10, 2004

(65) Prior Publication Data

US 2006/0163467 A1    Jul. 27, 2006

(30) Foreign Application Priority Data

Nov. 22, 2002  (GB) ................................. 0227267.2

(51) Int. Cl.
*G01V 5/04*       (2006.01)
*G01V 5/08*       (2006.01)

(52) U.S. Cl. .................................. 250/259; 250/269.1
(58) Field of Classification Search ................. 250/259, 250/269.1
See application file for complete search history.

(56) References Cited

U.S. PATENT DOCUMENTS 3,173,293 A * 3/1965 Eckels ..................... 73/152.19

(Continued)

FOREIGN PATENT DOCUMENTS

EP       0 461 321 A1    6/1990

(Continued)

OTHER PUBLICATIONS

Ammann et al Groundwater pollution by roof runoff infiltration evidenced with multi-tracer experiments Water Research 37, pp. 1143-1153, 2003.

(Continued)

*Primary Examiner*—David Porta
*Assistant Examiner*—Mindy Vu
(74) *Attorney, Agent, or Firm*—Vincent Loccisano; Steven Gahlings; James McAleenan

(57) ABSTRACT

The invention concerns an apparatus for analysing water chemistry. According to the invention, the apparatus is adapted to operate downhole and comprises a colouring agent supply device for supplying a colouring agent to a water sample, the colour of the water sample thus supplied being indicative of the water sample chemistry, and a colorimetric analyser arranged to determine the colour of the water sample.

11 Claims, 2 Drawing Sheets

U.S. PATENT DOCUMENTS

| | | | | |
|---|---|---|---|---|
| 3,407,042 | A | * | 10/1968 | Slentz .................. 436/30 |
| 3,851,171 | A | * | 11/1974 | Saniford et al. ............ 250/259 |
| 5,128,882 | A | | 7/1992 | Cooper et al. |
| 5,335,067 | A | * | 8/1994 | Prather et al. .............. 356/436 |
| 6,268,911 | B1 | | 7/2001 | Tubel et al. |
| 6,343,507 | B1 | | 2/2002 | Felling et al. |
| 6,476,384 | B1 | | 11/2002 | Mullins et al. |
| 2002/0108910 | A1 | | 8/2002 | Lyon |

FOREIGN PATENT DOCUMENTS

| | | |
|---|---|---|
| GB | 2 362 462 A | 11/2001 |
| WO | 99/00575 | 1/1999 |
| WO | 01/73424 A1 | 10/2001 |

OTHER PUBLICATIONS

Andrews et al Quantifying contamination using color of crude and condensate Oilfield Review 13 (3) pp. 24-43, Autumn 2001.

Bates Determination of pH: Theory and Practice, chapter 6, John Wiley, 1964.

Langmuir Aqueous Environmental Geochemistry Chapter 1, section 1.6.2, Prentice Hall, 1997.

Langmuir Aqueous Environmental Geochemistry Chapter 4, section 4.2, Prentice Hall, 1997.

Morris et al Using optical fluid analysis to evaluate downhole fluid sample contamination pp. 283-295. Presented at the SPE European Petroleum Conference, The Hague, The Netherlands, Oct. 1998.

Sandell Colorimetric Determination of Traces of Metals $2^{nd}$ edition, pp. 193-195, Interscience Publishers, 1950.

Sandell Colorimetric Determination of Traces of Metals $2^{nd}$ edition, pp. 242-249, Interscience Publishers, 1950.

Vogel Text-book of Quantitative Inorganic Analysis $3^{rd}$ edition, chapter 10, John Wiley, 1961.

Vogel Text-book of Quantitative Inorganic Analysis $3^{rd}$ edition, chapter 10, p. 803, John Wiley, 1961.

Vogel Text-book of Quantitative Inorganic Analysis $3^{rd}$ edition, chapter 1.30, p. 59, John Wiley, 1961.

* cited by examiner

APPARATUS AND METHOD FOR ANALYSING DOWNHOLE WATER CHEMISTRY

FIELD OF THE INVENTION

The present invention relates to an apparatus and method for downhole water chemistry analysis.

BACKGROUND OF THE INVENTION

Well operators commonly need to understand downhole water chemistry to help them decide production strategies and determine corrosion rates, scale formation rates, formation geochemistry etc.

More specifically, the pH and qualitative/quantitative analysis of the presence of specific ions in downhole water are often required.

Conventionally, water chemistry measurements are performed in the laboratory on fluid samples retrieved from below ground. However, water chemistry is not often preservable over the temperature and pressure changes typically induced by transportation from subterranean locations to the surface, and so a chemistry measurement of a sample collected for laboratory analysis will not always provide a result that can be related to the downhole value. Consequently, the water chemistry measured in the laboratory may vary significantly from that existing downhole.

SUMMARY OF THE INVENTION

An object of the present invention is to provide a more reliable analysis of downhole water chemistry.

Accordingly, in a first aspect, the present invention provides an apparatus for analysing water chemistry, the apparatus being adapted to operate downhole and comprising:

a colouring agent supply device for supplying a colouring agent to a water sample, the colour of the water sample thus supplied being indicative of the water sample chemistry, and a calorimetric analyser arranged to determine the colour of the water sample.

An advantage of the apparatus is that it allows in situ analysis to be performed, thereby avoiding the problems associated with transporting water samples to the surface. The present invention is at least partly based on the realisation that colorimetric analysis is a technique that can be adapted for performance downhole, i.e. in relatively demanding and hostile conditions.

In one embodiment the apparatus is installed downhole (e.g. in a hydrocarbon well or an aquifer).

Preferably the calorimetric analyser is connected to a processor for determining the water sample chemistry from the colour of the water sample. The processor may also be adapted for use downhole, or alternatively it may be intended for remote installation e.g. at the surface. For example the processor may be a suitably programmed computer.

The water sample colour may be indicative of e.g. water pH or a selected ion concentration level.

In one embodiment the calorimetric analyser comprises a spectrometer. An advantage of a spectrometer-based approach to colour analysis is that it has the potential to provide fast answers to questions of pH, corrosion chemistry and scale formation, which can be crucial for deciding e.g. completion design and materials and scale treatment programs.

A further aspect of the present invention provides for the use of the apparatus of the previous aspect for in situ analysis of downhole water chemistry.

In another aspect the present invention provides a method for analysing downhole water chemistry, the method comprising the steps of:

(a) supplying a colouring agent to a downhole water sample, the colour of the water sample thus supplied being indicative of the water sample chemistry, and (b) determining the colour of the water sample, wherein steps (a) and (b) are performed in situ.

In another aspect the present invention provides a method for monitoring contamination of downhole water, the method comprising the steps of:

(a) adding a tracer agent to a fluid which is a potential contaminant of the downhole water, (b) supplying a colouring agent to a sample of the downhole water, the colour of the water sample thus supplied being indicative of the presence of the tracer agent, and (c) determining the colour of the water sample, wherein steps (b) and (c) are performed in situ.

The potential contaminant may be drilling mud filtrate. The downhole water may be either connate or injected water.

BRIEF DESCRIPTION OF THE DRAWINGS

Specific embodiments of the present invention will now be described with reference to the following drawings in which.

DETAILED DESCRIPTION OF THE INVENTION

In general terms, the present invention relates to downhole colorimetric analysis. A preferred approach for the determination of pH and detection of the presence of specific ions involves injecting a specific indicator or reagent into a sample of water and determining the resulting colour of the fluid with an optical spectrometer.

Ions of interest for detection include those of Ca, Ba, Sr, Al, Cl, F, Fe, Mg, K, Si, Na, and ions containing sulphur and carbon (for example carbonate, bicarbonate, sulphate). Use of colorimetric and spectrometric analysis along with procedures and reagents required to determine the presence/ quantity of some of these ions have been described in the literature (Vogel, A. I., *Text-Book of Quantitative Inorganic Analysis*, 3$^{rd}$ Edition, Chapter 10, John Wiley, 1961; Sandell E. B., *Colorimetric Determination of Traces of Metals*, 3$^{rd}$ Edition, Interscience Publishers, 1959). However, we propose, for the first time, the application of these methods, in a downhole environment, to the analysis of downhole water as found in oil and gas fields, as well as aquifers. Typical temperatures and pressures found in a downhole environment are in the range of 125° C. and 10,000 psi, respectively; however they can go up to as high as 175° C. and 20,000 psi.

To perform quantitative measurements of pH or ion concentration, the optical absorption of the unknown species can be determined either relative to a standard solution (which could be the water sample itself prior to indicator/reagent addition) or with a stable and previously calibrated spectrometer.

Desirably, the spectrometer should be capable of operating over the visible spectrum of 400 to 760 nm, which is from ultraviolet to infrared respectively.

In one embodiment we propose fitting a known Modular Dynamic Tester (MDT) with a Live Fluid Analyzer (LFA) module (R. J. Andrews et al., Oilfield Review, 13(3), 24-43). The LFA would inject coloured indicators to the water flowing through the MDT so that pH can be determined. It can also add suitable reagents to the water for determination of the presence/concentration of selected ions.

Figure 1:
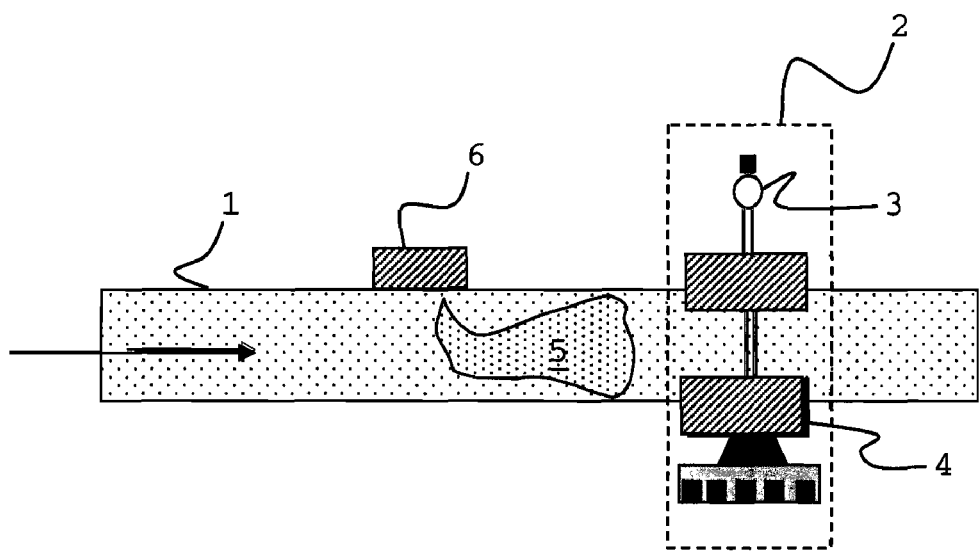
FIG. 1 shows a schematic diagram of a Live Fluid Analyser installed on a flow line.

FIG. 1 shows a schematic diagram of the LFA installed on a flow line 1, the other parts of the MDT not being shown. An arrow indicates the direction of water flow in the flow line. The LFA has an upstream dye injector 6 and a downstream optical analyser 2. The analyser comprises a light source 3 on one side of the flow line and a facing light detector 4 on the opposite side of the flow line. When a preselected indicator or reagent 5 is injected into flow line it mixes with the water and is carried downstream to the analyser, whereupon the detector generates a signal indicative of the colour of the water. If required a mixer, not shown in the figure, such as a double helix, can be used to promote mixing of the water and dye. A processor (not shown) then determines the water chemistry from the signal e.g. using approaches discussed below.

Such colorimetric analysis also allows contamination of formation water by water-based mud filtrate to be detected. This can be achieved by suitable indicator/reagent selection such that the water-based mud filtrate and formation water generate different respective colours.

Another option is to add a tracer ion or other species (for example, nitrate, iodide or thiocyanate ions) to the drilling fluid. A reagent can then be used in the LFA, which produces a colour change in the presence of the tracer so that the tracer can be detected and preferably quantified. In this way real-time monitoring of connate water for contamination by the filtrate can be achieved.

A possible reagent for detecting iodide is the iodobismuthite ion, formable from a solution of bismuth in dilute sulphuric acid. This ion gives a yellow orange colouration and is sensitive up to 1% iodide (Vogel, A. I., *Text-Book of Quantitative Inorganic Analysis*, 3$^{rd}$ Edition, Chapter 10, p803 John Wiley, 1961).

We now describe how indicator colouration can be used to measure pH. However, similar considerations apply when the colour of any reagent is being used to measure ion concentration.

For pH measurements the choice of indicator depends to a significant extent on the accuracy with which the pH is required. As an example, we take a universal indicator, a volume of which has been injected into the sample flowline upstream of the optical detector. The indicator volume is determined by the flow rate of the water and intensity of the colour and is usually a small fraction of the total volume. The universal indicator may be formed e.g. from a mixture of 0.2 g of phenolphthalein, 0.4 g methylred, 0.6 g dimethylazobenzene, 0.8 g bromothymol blue, and 1 g of thymol blue in 1 l ethanol. To this solution is added NaOH(aq) until the solution appears yellow. The colours of the solution as a function of pH are listed in the table below (Vogel, A. I., *Text-Book of Quantitative Inorganic Analysis*, 3$^{rd}$ Edition, Chapter 1.30, p 59 John Wiley, 1961).

| | pH | | | | | |
|---|---|---|---|---|---|---|
| | 2 | 4 | 6 | 8 | 10 | 12 |
| Colour | Red | Orange | Yellow | Green | Blue | Purple |

An alternative is to use a plurality of indicators each of which is specific to a respective pH range. This may result in a more precise determination of pH.

The pH of an unknown solution may be obtained using the equation below (R. G. Bates, *Determination of pH: Theory and Practice*, Chapter 6, John Wiley, 1964):

$$pH = pKa + \log\frac{\gamma_B}{\gamma_A} + \log\frac{B}{A} \quad (1)$$

where Ka is the thermodynamic equilibrium constant for the indicator and is a function of temperature; A and B are the respective fractions of the acid and base forms of the indicator; and $\gamma_A$ and $\gamma_B$ are respective activity coefficients of the acid and base forms of the indicator, and depend on ionic strength of the solution and temperature. Both Ka and activity coefficients could be weak functions of pressure as well.

The fraction of the indicator that exists in the acid form (A) and base form (B) may be measured spectroscopically. The absolute concentration of the dye does not appear in the equation and hence the pH calculation is independent of the volume of dye injected or the flow rate of the water stream as long as the concentration is such that Beer's law is satisfied. The functional dependence of Ka on temperature (T) has been studied and measured for a number of reactions and a general equation that can describe this dependence is (D. Langmuir, *Aqueous Environmental Geochemistry*, Chapter 1, Section 1.6.2, Prentice Hall, 1997):

$$\log Ka = a + bT + \frac{c}{T} + d\log T + eT^2 \quad (2)$$

The parameters in this equation may be obtained by calibration in the laboratory over the desired temperature range using standard buffers of known pH. Dependence on pressure may also be obtained through experimental calibration if necessary. Several models have been proposed for activity coefficient estimation. For example, the Debye-Huckel equation is commonly used for low ionic strength solutions and the Pitzer model at higher ionic strengths (D. Langmuir, *Aqueous Environmental Geochemistry*, Chapter 4, Section 4.2, Prentice Hall, 1997). Ionic strengths can be derived from downhole water sample conductivity/resistivity measurements as is done in the MDT or alternatively from other wireline measurements such as resistivity logs. For very dilute solutions and/or for acid and base forms that have similar behaviours, the activity coefficient term may be neglected. Thus equation (1) provides a means for determining pH under downhole conditions for most temperatures, pressures and ionic strengths encountered in practice.

Figure 2A:
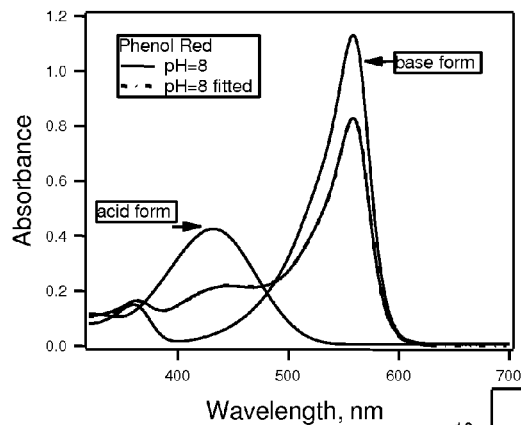
FIG. 2a shows the room temperature absorbance spectra of (a) the acid form of phenol red, (b) the base form of phenol red, (c) phenol red in a pH 8 solution, and (d) a weighted sum of the acid and base form spectra fitted to the pH 8 solution absorbance spectrum.

As an example, FIG. 2a shows the room temperature absorbance spectra of (a) the acid form of phenol red and (b) the base form of phenol red. The acid form has a peak at about 432 nm and the base form at about 559 nm. FIG. 2a also shows (c) the measured absorbance spectrum of phenol red in a pH 8 solution, and (d) a weighted sum of the acid and base form spectra fitted to the measured absorbance spectrum, the weightings providing the base and acid fraction of phenol red in the pH 8 solution.

Figure 2B:
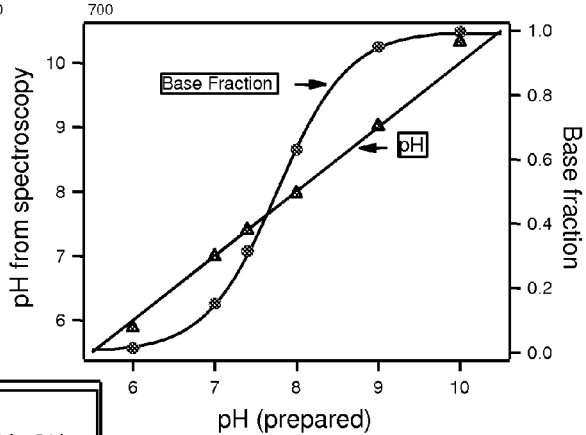
FIG. 2b shows graphs of base fraction of phenol red (right hand vertical axis) and calculated pH (left hand vertical axis) as functions of prepared solution pH.

Similar analyses can be performed for solutions prepared with different pH levels. FIG. 2b shows a graph of base fraction of phenol red (right hand vertical axis) as a function of prepared solution pH (horizontal axis). Using equation (1) it is then possible to, calculate the pH of each solution. The calculated pH values (left hand vertical axis) are also plotted on FIG. 2b. They show that, in this example, pH determined by spectroscopy is highly accurate for phenol red base fractions in the range of about 0.05 to 0.95 corresponding to pH values from 6.5 to 9. The range of pH measurement can be increased to 6 to 9.5 if the acid and base fractions can be spectroscopically detected at lower levels of 0.02.

The accuracy of the pH measurement is higher when the pH is close to the pKa value and decreases when the pH departs from the pKa. Thus, if the likely pH range is known, an indicator can be selected which has a pKa value such that a desired level of accuracy can be achieved. A combination of indicators may be chosen to cover the pH range typically expected in formation waters. In this way, provided the optical analyser has suitable wavelength windows to observe the colour changes, the pH can be obtained to within a value of a few tenths. Depending on how the indicators interact with each other, multiple injectors in series or parallel may be used for the different indicators or a single injector with a mixed indicator solution may be deployed.

The analysis may be performed using a stable and calibrated colorimeter/spectrophotometer. Alternatively, the absorbance spectra of the water sample in the flow line prior to indicator injection can yield the baseline. Yet another option is to use a reference solution to calibrate the colorimeter/spectrophotometer. The last two options provide a means of compensating for any possible inherent water colour.

Further improvements may be obtained if a series of buffer reference solutions are supplied, each differing in pH e.g. by about 0.2 and covering the range around the expected pH value. Indicator is then added to known volumes of the buffer solution and the water sample and the colours compared to determine the pH. To ensure accuracy, preferably the water sample is a captured sample.

Figure 3A:
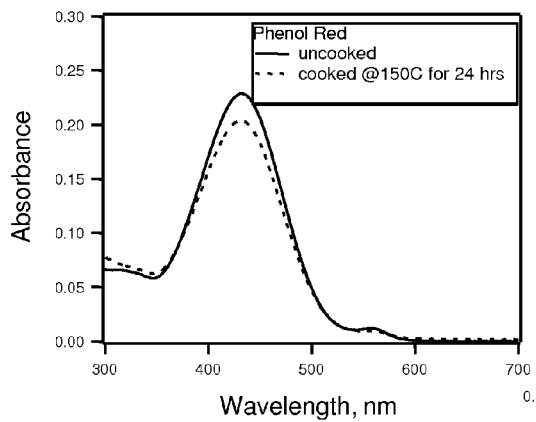
FIG. 3a shows the room temperature absorbance spectra obtained from (a) phenol red in deionised water and (b) phenol red in deionised water after heat treatment at 150° C. for 24 hours.

For downhole use, the indicator should be stable and chemically active at the temperatures expected downhole. As an example, FIG. 3a shows the room temperature absorbance spectra obtained from (a) phenol red in deionised water and (b) phenol red in deionised water after heat treatment at 150° C. for 24 hours. The heat treatment results in only a 10% loss in absorbance, demonstrating that the phenol red indicator can survive prolonged exposure to temperatures of up to 150° C.

Figure 3B:
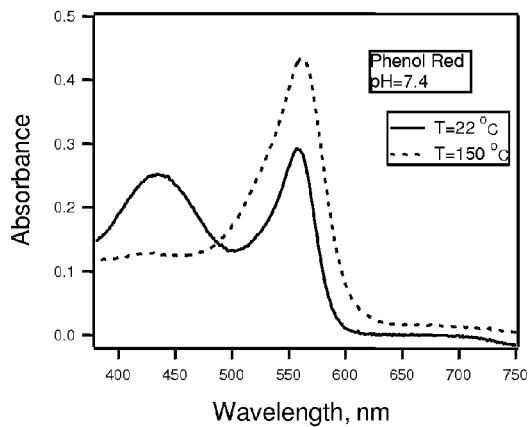
FIG. 3b shows the absorbance spectra obtained from (a) phenol red in a pH 7.4 buffer solution at 22° C. and (b) phenol red in the pH 7.4 buffer solution at 150° C.

However, it may be necessary to calibrate each indicator/reagent for the different temperatures and ionic strengths to which it will be exposed downhole. FIG. 3b shows the spectra obtained from (a) phenol red in a 7.4 pH buffer solution at 22° C. and (b) phenol red in the 7.4 pH buffer solution at 150° C. At 150° C. the phenol red is still chemically active, the increase in base fraction at the higher temperature being due to changes in pKa and the pH of the buffer solution with temperature.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. An apparatus for analysing water chemistry, the apparatus being adapted to operate downhole and comprising:
    a flowline for flowing a water sample through;
    a colouring agent injection device coupled with the flowline and configured for injecting a colouring agent into the water sample flowing in the flowline, the colour of the water sample and the injected colouring agent being indicative of the water sample chemistry; and
    a colorimetric analyser coupled with the flowline downstream of the colouring agent injection device and arranged to determine the colour of the water sample.

2. An apparatus according to claim 1 which is installed downhole.

3. An apparatus according to claim 1 wherein the colorimetric analyser is operably connected to a processor which determines the water sample chemistry from the colour of the water sample.

4. An apparatus according to claim 1, wherein the colorimetric analyser comprises a spectrometer.

5. An apparatus of claim 1, wherein said apparatus is used for in situ analysis of downhole water chemistry.

6. The apparatus according to claim 1, further comprising:
    a mixer disposed downstream of the injection device for mixing the water sample and the colouring agent.

7. The apparatus according to claim 6, wherein the mixer comprises a double helix.

8. The apparatus according to claim 1, wherein the colorimetric analyzer comprises a visible spectrum spectrometer.

9. A method for analysing downhole water chemistry, the method comprising the steps of:
    (a) flowing a water sample through a flowline;
    (b) injecting a colouring agent into the water sample flowing in the flowline, the colour of a mixture of the water sample and the colouring agent being indicative of the water sample chemistry; and
    (c) determining the colour of the water sample, wherein steps (a), (b) and (c) are performed in situ.

10. The method according to claim 9, further comprising mixing the water sample and the colouring agent.

11. A method for monitoring contamination of downhole water, the method comprising the steps of:
    (a) adding a tracer agent to a fluid which is a potential contaminant of the downhole water,
    (b) flowing a sample of the downhole water through a flowline;
    (c) supplying a colouring agent to a the sample of the downhole water flowing in the flowline, the colour of the water sample mixed with the colouring agent being indicative of the presence of the tracer agent; and
    (d) determining the colour of the water sample,
    wherein steps (b), (c) and (d) are performed in situ.

* * * * *